(12) United States Patent
Davies (10) Patent No.: US 6,516,798 B1
(45) Date of Patent: Feb. 11, 2003

(54) METHOD OF BREATHING TRACHEALLY

(76) Inventor: Timothy A. Davies, 3701 Fillmore St., #31, Riverside, CA (US) 92505

( * ) Notice: Subject to any disclaimer, the term of this patent is extended or adjusted under 35 U.S.C. 154(b) by 0 days.

(21) Appl. No.: 09/520,052

(22) Filed: Mar. 7, 2000

(51) Int. Cl.[7] .............................................. A62B 18/08
(52) U.S. Cl. ............................ 128/201.13; 128/207.14; 128/203.16
(58) Field of Search ................. 128/201.13, 206.22, 128/207.14, 200.24, 203.12, 203.16, 204.18, 205.27, 205.28, 898

(56) References Cited

U.S. PATENT DOCUMENTS

| | | | | |
|---|---|---|---|---|
| 3,603,313 A | * | 9/1971 | Arblaster | 128/206.22 |
| 4,090,513 A | * | 5/1978 | Togawa | 128/212 |
| 5,022,394 A | * | 6/1991 | Chmielinski | 128/207.14 |
| 5,485,837 A | * | 1/1996 | Solesbee et al. | 128/207.17 |
| 5,546,930 A | * | 8/1996 | Wikefeldt | 128/201.13 |
| 5,901,705 A | * | 5/1999 | Leagre | 128/207.14 |
| 6,095,135 A | * | 8/2000 | Clawson et al. | 128/201.13 |
| 6,109,259 A | * | 8/2000 | Fitzgerald | 128/200.26 |

* cited by examiner

Primary Examiner—Glenn K. Dawson
(74) Attorney, Agent, or Firm—Timothy Thut Tyson; Ted Masters; Freilich, Hornbaker & Rosen (57) ABSTRACT

A tracheal humidification system (20) includes a filter (26) for humidifying the air being breathed by the patient. The filter (26) is disposed in an uppermost portion (24) of a breathing path (22). At least one secretion path (28) including a drain tube (30) is provided for collecting secretions (512) from the patient. Filter (26) is disposed above the secretion path (28), so that the secretions (512) are prevented from contacting and clogging filter (26).

2 Claims, 7 Drawing Sheets

METHOD OF BREATHING TRACHEALLY

TECHNICAL FIELD

The present invention pertains generally to tracheal surgery or tracheotomy, and in particular to an improved tracheal humidification system. The system of the present invention employs different breathing and secretion paths, and further elevates the breathing filter so that it cannot be contaminated by secretions.

BACKGROUND ART

After having a tracheotomy, a patient is fitted with a ventilator system to facilitate healing and recovery. One of the functions of the ventilator system is to trap bronchial secretions. Another feature of the ventilator system is to humidify the air that the patient breaths to reduce drying of the mucus. For years the ventilator systems injected aerosolized water which was directed at the trachea. While this time-tested method of providing humidification worked, it has inherent drawbacks that could not be overcome. Some of drawbacks are:

Current aerosols require high-flow oxygen and greatly increase the cost of caring for the patient.

Tubing must be constantly drained to provide free airflow. This is labor-intensive.

The environment is kept wet at the bedside by the constant bombardment of moisture.

The open nature of the tracheal aerosol leaves the patient susceptible to infection by airborne and contact sources.

The high particulate water content of the air being delivered to the patient is suspected as being partially responsible for the hyper-production of secretions in the patient with the tracheotomy.

For those facilities that do not have piped-in air, those patients who require humidification must be either placed on oxygen or noisy, hot compressors placed in their rooms.

Current aerosols are noisy, and high noise levels do not provide for a good environment of care.

The open nature of the aerosol delivery system also exposes the caregiver, physician and family to possible exposure as patients cough and secretions are expelled into the surrounding environment.

Contamination of the surrounding environment opens the possibility for nosocomial infections, especially for those patients in close proximity.

Secretions are expelled and tend to collect around the trachea, soiling linen, tracheal dressings etc., and increasing nursing time at the bedside and the overall cost of care.

Figure 1:
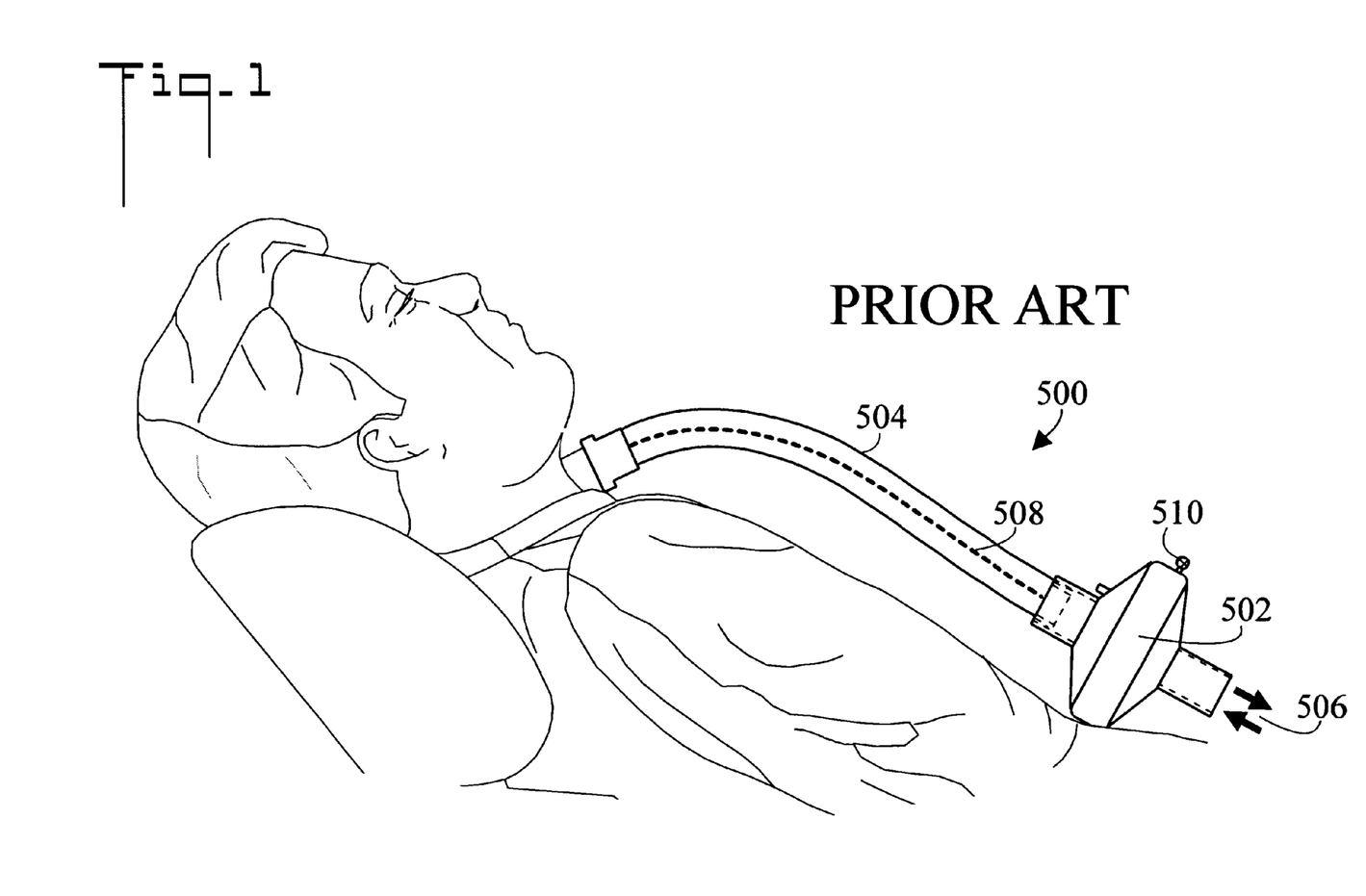
FIG. 1 is a prior art tracheal humidification system wherein the breathing path and secretion path are one in the same.
Figures 2, 3:
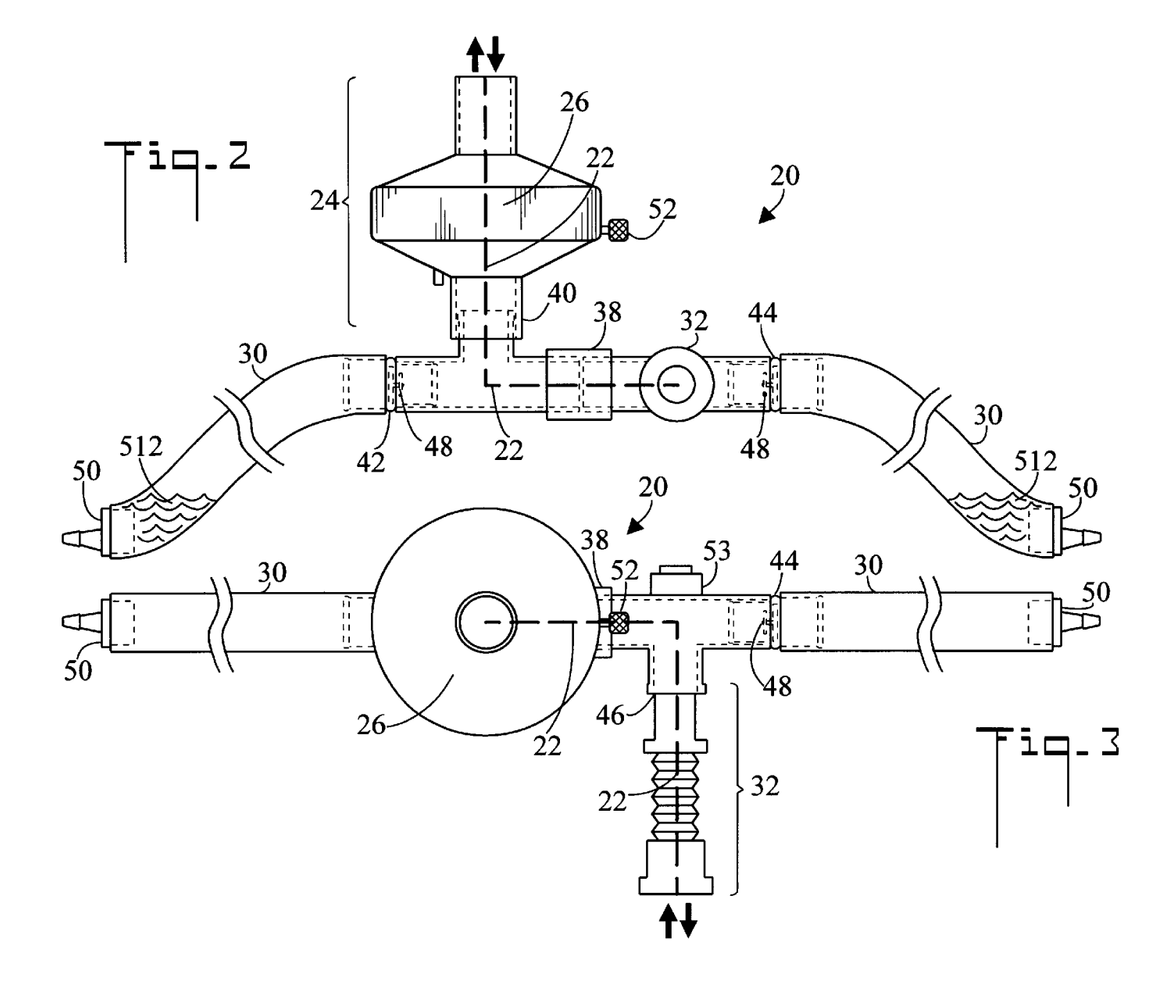
FIG. 2 is a front elevation view of a tracheal humidification system in accordance with the present invention.
FIG. 3 is a top plan view of the tracheal humidification system.

About 10 years ago heat moisture exchangers (HMEs) and hydroscopic condensing humidifiers (HCHs) were developed as an alternative to conventional means of humidification. These systems have been used on mechanically ventilated patients with great success by using the patients' own humidity and moisture but have been used only rarely on naturally ventilated patients due to their tendency to clog with secretions (refer to FIG. 1). The system 500 includes a ARC Thermoflo™ Medical HCH filter 502 and a flexible hose 504 which connects the filter 502 to the trachea of the patient. Flexible hose 504 comprises both the breathing path (airway) 506 and the secretion path 508 for bronchial secretions. The system 500 can also include a input port 510 for low flow oxygen. These systems 500 have reduced costs, decrease infection rates and provided many other savings for the medical facility. However, these systems 500 are troublesome in that the high volume of secretions associated with a tracheotomy clog the filter 502 thereby making breathing difficult. If the filter is not continuously monitored and regularly replaced, near-complete occlusion of the airway 506 could result.

DISCLOSURE OF INVENTION

The present invention is directed to an improved tracheal humidification system which overcomes the disadvantages of the prior art. A preferred name for the present invention is the "Safe and Silent" Waterless System. In the present invention the HCH or HME filter is removed from the path of secretions. That is, the breathing and secretion paths or passages are different. By removing the filter from the path of secretions, the filters now perform as designed, capturing humidity and warmth while staying free of secretions that increase resistance and make breathing difficult. The patient breathes through a closed system, exhaling through the HCH or HME filter, which captures the patient's own heat and humidity. The patient then inhales and the entrained air recaptures the moisture and heat. The present invention also provides minimal deadspace and maximal drain for expelled secretions.

The present invention also includes baffles which minimize the mixing of air between the breathing path or airway and the bilateral secretion drain tubes. This minimizes mixing of $CO_2$ trapped in the drain tubes. The secretion tubes have a unique suction end cap which provides for the clearance of expelled secretions, while maintaining the integrity of a closed system. The present invention also has a closed suction catheter which provides suctioning while completing the emphasis on a closed system.

The present invention has the following advantages over current methods of humidification:

1. The closed system means that the patient is breathing air that has been filtered and thus their exposure is reduced. The closed system consists of a plurality of tubular members connected by rotatable joints. In a preferred embodiment, the tubular members are fabricated from transparent plastic to that the inside of the system may be visually inspected.

2. Expelled secretions are captured in a drain tube and therefore the surrounding environment is not contaminated, reducing exposure to the staff, visitors, etc.

3. No accumulation of secretions on the patient means less time for care at the bedside, reduced linen usage, and better care of the environment.

4. The system of the present invention is passive and therefore completely silent. Current alternatives are noisy and cause the facility noise level to be exceptionally high.

5. The system employs low-flow $O_2$. Oxygen costs can be greatly reduced.

6. By employing use of a closed suctioning system as well, costs for suctioning supplies can be greatly reduced.

7. The system is portable.

8. The system reduces waste disposal.

9. Finally, the closed system of the present invention provides for fewer infections. Patient receiving continuous, mechanically assisted ventilation have 6–21 times the risk of acquiring nosocomial pneumonia compared to patients not receiving ventilatory support.

In accordance with a preferred embodiment of the invention, a tracheal humidification system for placement upon the chest of a patient who is reclining on his/her back, includes (1) a filter for humidifying air being breathed by the patient, the filter is disposed in an uppermost portion of a breathing path, and (2) at least one secretion path for collecting secretions from the patient. The filter is disposed above the secretion path, so that the secretions are prevented from contacting and contaminating the filter.

In accordance with an important aspect of the invention, the breathing path is oriented in a substantially vertical position.

In accordance with an important feature of the invention, the breathing path has a flexible tracheal connecting portion for connecting to a patient.

In accordance with another important aspect of the invention, the upper portion and filter are rotatable about a substantially vertical plane with respect to the tracheal connecting portion.

In accordance with another important feature of the invention, the secretion path includes a drain tube for collecting the secretions of the patient.

In accordance with another important aspect of the invention, the secretion path has a baffle to restrict the flow and mixing of air between the breathing path and the drain tube.

In accordance with another important feature of the invention, the drain tube has an end portion having a selectively closable and openable secretion clearance cap.

In accordance with another important feature of the invention the tracheal humidification system is closed.

Other features and advantages of the present invention will become apparent from the following detailed description, taken in conjunction with the accompanying drawings, which illustrate, by way of example, the principles of the invention.

MODES FOR CARRYING OUT THE INVENTION

Referring initially to FIGS. 2–4, and 8, there are illustrated side elevation, top plan, end elevation, and reduced perspective views respectfully of a tracheal humidification system in accordance with the present invention, generally designated as 20. Tracheal humidification system 20 includes a breathing path 22 (shown by a heavy dashed line) having an uppermost portion 24 which is oriented in a substantially vertical position. The patient breathes in and out through breathing path 22. The uppermost portion 24 includes a filter 26 and filter housing. The tracheal humidification system 20 also includes at least one secretion path 28 (shown in a heavy dotted line in FIGS. 5–7). In a preferred embodiment two bilateral secretion paths 28 are utilized which include two flexible drain tubes 30. The flexible drain tube portion 30 of the secretion path 28 is downwardly oriented so as to collect and capture the secretions 512. In the shown in use configuration, filter 26 is disposed above secretion path 28 so that as the patient breathes, secretions 512 cannot contact and clog filter 26.

Breathing path 22 also includes a tracheal connecting portion 32 for connecting to the trachea of the patient. In a preferred embodiment tracheal connecting portion 32 is flexible to reduce stress upon the trachea.

Figure 4:
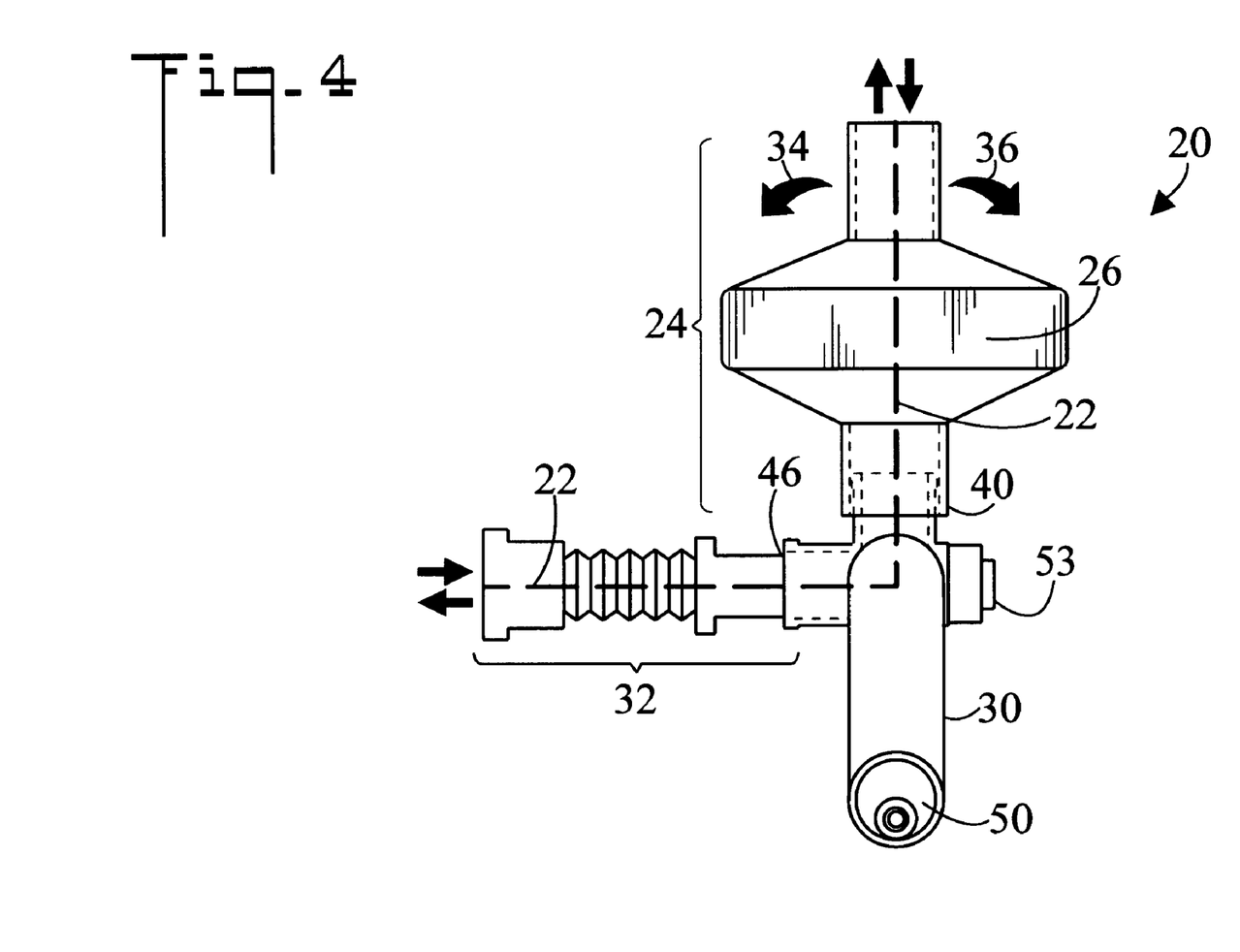
FIG. 4 is an end view of the tracheal humidification system.
Figures 5, 6:
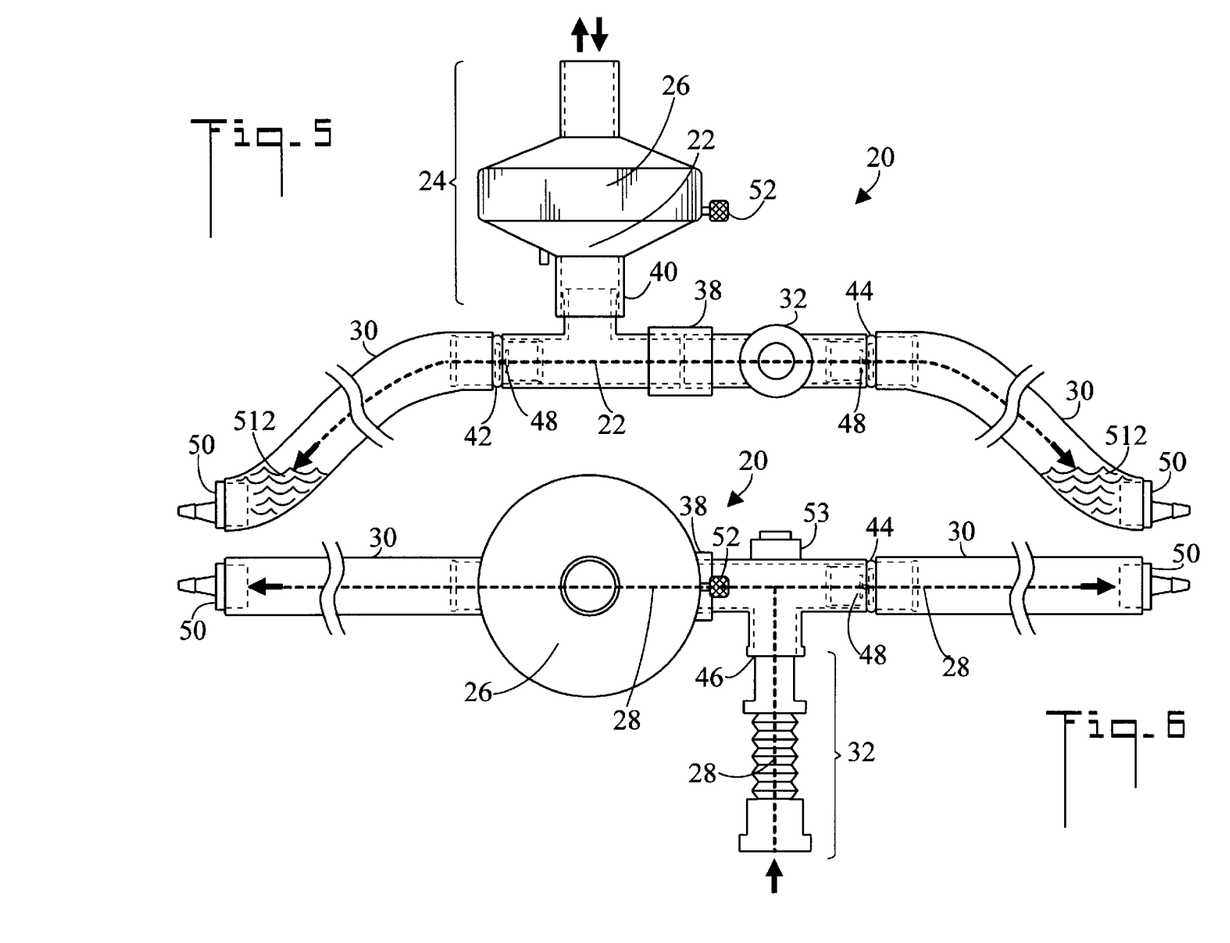
FIG. 5 is a front elevation view of the tracheal humidification system showing the secretion path.
FIG. 6 is a top plan view of the tracheal humidification system showing the secretion path.
Figure 7:
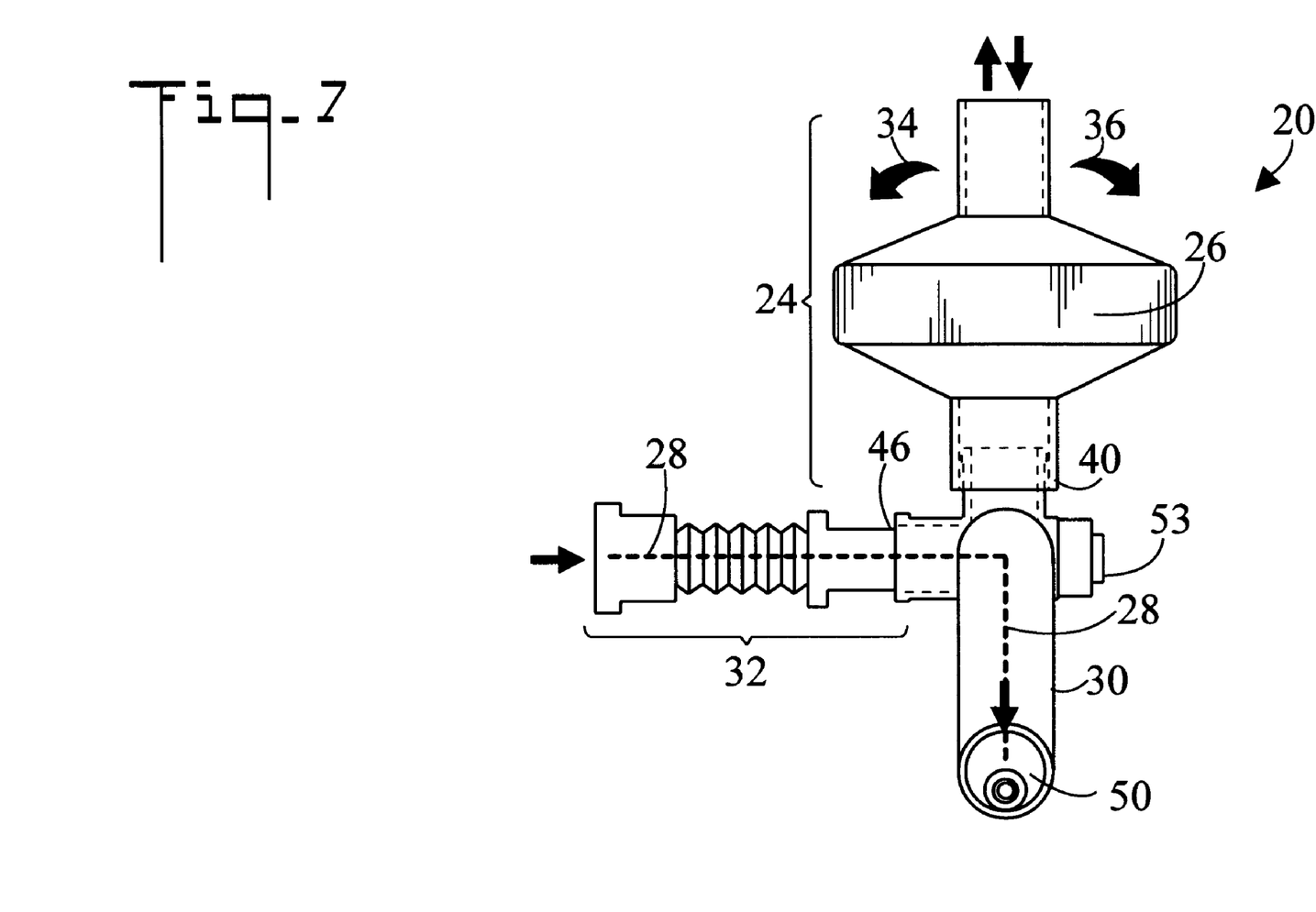
FIG. 7 is an end view of the tracheal humidification system showing the secretion path.
Figure 8:
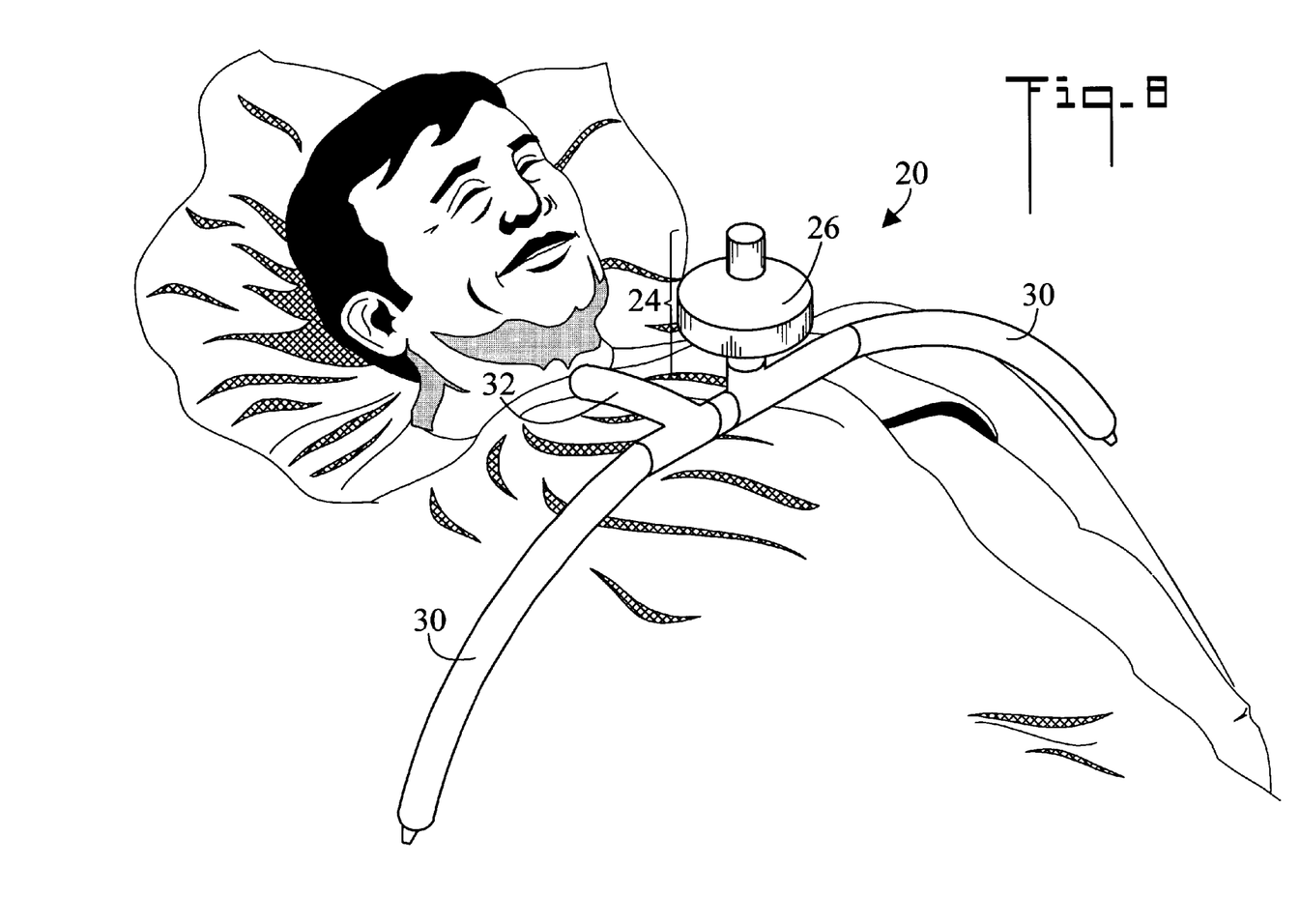
FIG. 8 is a reduced simplified perspective view of the tracheal humidification system being used by a patient.
Figure 9:
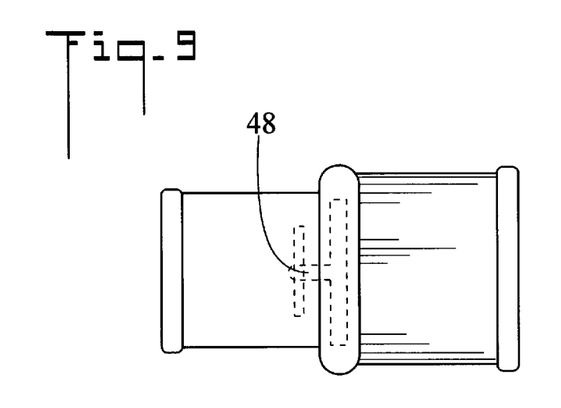
FIG. 9 is an enlarged side elevation view of a baffle assembly.
Figure 10:
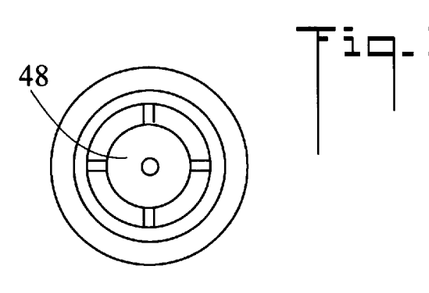
FIG. 10 is an enlarged end view of the baffle assembly.
Figure 11:
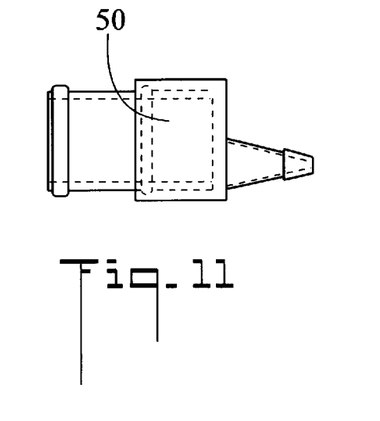
FIG. 11 is an enlarged side elevation view of a secretion clearance cap.
Figure 12:
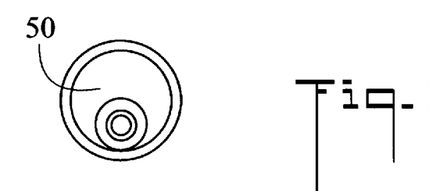
FIG. 12 is an enlarged end view of the secretion clearance cap.

Referring to FIGS. 4 and 7, it is noted that uppermost portion 24 and filter 26 are rotatable about a substantially vertical plane in directions 34 and 36 with respect to tracheal connecting portion 32. This feature of the present invention permits uppermost portion 24 to always be placed in a substantially vertical position when tracheal humidification system 20 is installed on a patient. This adjustment is made possible by rotatable barrel adapter 38. Similarly, joints 40, 42, 44, and 46 are all rotatable so the all useful angles can be achieved. Secretion path 28 includes a baffle 48 to restrict the flow of air (also refer to FIGS. 9 and 10). Baffle 48 minimizes the mixing of $CO_2$ trapped in drain tubes 30 with the air being breathed by the patient through breathing path 22. Flexible drain tube 30 has an end portion which has a selectively closable and openable secretion clearance cap 50 (also refer to FIGS. 11 and 12). Clearance cap 50 can be rotated to align two apertures which allow removal of secretions 512 and then re-closed to maintain the integrity of the closed system. Secretions 512 may also be sucked out with a vacuum.

Tracheal humidification system 20 also includes a port 52 for injecting oxygen, and a port 53 for cleaning the inside of the device.

The tracheal humidification system 20 of the present invention is used as follows:

1. The patient assumes a generally reclining position upon his/her back;
2. The tracheal humidification system 20 is placed upon the chest of the patient;
3. The drain tubes 30 of the secretion path 28 are then downwardly oriented;
4. The tracheal connecting portion 32 is then installed in the trachea of the patient;
5. The uppermost portion 24 is rotated to a substantially vertical position;
6. The secretion clearance cap 50 is periodically opened to clear secretions 512 from the secretion path 28; and,
7. The secretion clearance cap 50 is then reclosed to maintain the airtight integrity of the closed system.

The preferred embodiments of the invention described herein are exemplary and numerous modifications, dimensional variations, and rearrangements can be readily envisioned to achieve an equivalent result, all of which are intended to be embraced within the scope of the appended claims.

I claim:

1. A method for a patient to breath tracheally, comprising:

providing a tracheal humidification system including (1) a breathing path having an uppermost portion having a filter, (2) at least one secretion path having a drain tube, and (3) a tracheal connecting portion, said uppermost portion rotatable in a substantially vertical plane with respect to said tracheal connecting portion;

the patient assuming a generally reclining position upon his/her back;

placing said tracheal humidification system upon the chest of the patient;

downwardly orienting said drain tube;

installing said tracheal connecting portion in the trachea of the patient; and, rotating said uppermost portion to a substantially vertical position.

2. The method according to claim 1, further including:

said drain tube having a selectively closable and openable secretion clearance drain cap;

periodically opening said secretion clearance cap to clear secretions from said secretion path; and, reclosing said secretion clearance cap.

* * * * *